US006136530A

United States Patent [19]
Poduslo

[11] Patent Number: 6,136,530
[45] Date of Patent: *Oct. 24, 2000

[54] COMPOSITIONS AND METHODS FOR ASSESSING RISK FACTORS IN ALZHEIMER'S DISEASE

[75] Inventor: Shirley E. Poduslo, Lubbock, Tex.

[73] Assignee: Texas Tech University Health Sciences Center, Lubbock, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/757,223

[22] Filed: Nov. 27, 1996

Related U.S. Application Data

[60] Provisional application No. 60/007,738, Nov. 29, 1995.

[51] Int. Cl.⁷ .............................. C12Q 1/68; C12P 19/34
[52] U.S. Cl. .......................... 435/6; 436/501; 436/91.2; 436/811; 536/24.33
[58] Field of Search ................................ 435/6; 436/501, 436/503, 811, 91.2; 536/24.31, 24.33, 25.32

[56] References Cited

U.S. PATENT DOCUMENTS

| | | |
|---|---|---|
| 4,683,202 | 7/1987 | Mullis . |
| 5,434,050 | 7/1995 | Maggio et al. . |
| 5,441,870 | 8/1995 | Seubert et al. . |
| 5,508,167 | 4/1996 | Roses et al. . |

FOREIGN PATENT DOCUMENTS

| | | |
|---|---|---|
| WO 94/09155 | 4/1994 | WIPO . |
| WO 95/16791 | 6/1995 | WIPO . |

OTHER PUBLICATIONS

Smit et al, Biochem and Biophysical Research Communications, 152(3):1282–1288, 1988.
Yu et al, Am. J. Hum. Genet. 54:631–642, 1994.
Templeton, A.R, Genetics, 140:403–409, May 1995.
Poduslo et al, Neuroscience Letters, 201:81–83, 1995.
Poduslo et al, Society for Neuroscience, 21(1–3):1487, 1995.
Poduslo et al, Society for Neuroscience, 22(1–3):199, 1996.
Crawford et al, Neurobiology of Aging, 17(Suppl.):S124–S125, 1996.
Patentability Search for APOCI Allele.
New York Times, Nov. 1995 (exact date unknown).
Wall Street Journal, Aug. 15, 1995.
Andrew, et al., "DNA Analysis of Distinct Populations Suggests Multiple Origins for the Mutation Causing Huntington Disease," *Clin Genet*, 43:286–294, 1993.
Caracciolo, et al., "Lineage–Specific Requirement of c–abl Function in Normal Hematopoiesis," *Science*, 245:1107, 1989.
Chartier–Harlin, et al., "Apolipoprotein E4, ∈4 Allele as a Major Risk Factor for Sporadic Early and Late–Onset Forms of Alzheimer's Disease: Analysis of the 19q13.2 Chromosomal Region," *Human Molecular Genetics*, 3(4):568–574, 1994.

Farrer, L.A. and Cupples, L.A., "Estimating the Probability for Major Gene Alzheimer Disease," *Am. J. Hum. Genet.*, 54:374–383, 1994.
Frossard, et al., "Human Apolipoprotein CI (ApoC1) Gene Locus: BgII Dimorphic Site," *Nucleic Acids Research*, 15(3):1344, 1987.
Frossard, et al., "Human Apolipoprotein CI (apoC1) Gene Locus: DraI Dimorphic Site," *Nucleic Acids Research*, 15(4):1884, 1987.
Goddard, et al., "Toward Localization of the Werner Syndrom Gene by Linkage Disequilibrium and Ancestral Haplotyping: Lessons Learned from Analysis of 35 Chromosome 8p11.1–21.1 Markers," *Am. J. Hum. Genet.*, 58:1286–1302, 196.
Kamino, et al., "Genetic Association Study Between Senile Dementia of Alzheimer's Type and APOE/C1/C2 Gene Cluster," *Gerontology*, 42(Suppl 1) :12–19, 1996.
Lauer, et al., "Two Copies of the Human Apolipoprotein C–I Gene Are Linked Closely to the Apolipoprotein E Gene," *Journal of Biological Chemistry*, 263(15) :7277–7286, 1998.
Saiki, et al., "Primer–Directed Enzymatic Amplification of DNA with a Thermostable DNA Polymerase," *Science*, 239 :487–491, 1988.
Sanger, et al., "DNA Sequencing with Chain–Terminating Inhibitors," *Proc. Natl. Acad. Sci. USA*, 74(12) :5463–5467, 1977.
Schellenberg, et al., "Genetic Association and Linkage Analysis of the Apolipoprotein CII Locus and Familial Alzheimer's Disease," *Annals of Neurology*, 31(2) :223–227, Feb. 1992.
Sehayek, et al., "Mechanisms of Inhibition by Apolipoprotein C of Apolipoprotein E–Dependent Cellular Metabolism of Human Triglyceride–Rich Lipoproteins Through the Low Density Lipoprotein Receptor Pathway," *Journal of Biological Chemistry*, 266(27) :18259–18267, Sep. 1991.

(List continued on next page.)

*Primary Examiner*—Patricia A. Duffy
*Attorney, Agent, or Firm*—Denise L. Mayfield; Locke Liddell & Sapp LLP

[57] ABSTRACT

The presence of a restriction site in the gene for apolipoprotein CI (APOCI) is a risk factor for Alzheimer's disease. The invention involves determining the presence of the restriction site in biological samples from patients suspected to be at risk for Alzheimer's disease. The presence of the restriction site indicates that the patient may be at higher risk for the disease; those who are heterozygotes may be at intermediate risk; while those lacking the site are at a lesser risk for the disease. PCR amplification and the use of improved oligonucleotide primers specific to the region surrounding the restriction site as well as digestion with the restriction enzyme may be used to determine the presence of the site. APOCI provides a genetic marker for Alzheimer's disease that is distinct from APOE4. The methods disclosed provide a more accurate and definitive screening technique for the early identification of Alzheimer's disease compared to screening of APOE4 alone in some populations.

4 Claims, 4 Drawing Sheets

OTHER PUBLICATIONS

Shulman, et al., "The Complete Amino Acid Sequence of C–I (ApoLp–Ser), an Apolipoprotein from Human Very Low Density Lipoproteins," *Journal of Bological Chemistry*, 250(1) :182–190, Jan. 1975.

Simonet, et al., "Multiple Tissue–Specific Elements Control the Apolipoproten E/C–I Gene Locus in Transgenic Mice," *Journal of Biological Chemistry*, 266(14) :8651–8654, May 1991.

Smit, et al., "Apolipoprotein Gene Clustor on Chromosome 19: Definite Localization of the APOC2 Gene and the Polymorphic HpaI Site Associated with Type III Hyperlipoproteinemla,"*Human Genetics*, 78:90–93, 1998.

Strittmatter, et al., "Apolipoprotein E: High–Avidity Binding to β–Amyloid and Increased Frequency of Type 4 Allele in Late–Onset Familial Alzheimer Disease," *Proc. Natl. Acad. Sci. USA*, 90:1977–1981, Mar. 1993.

Nillesen, et al., "Human ApoCI HpaI Restriction Site Polymorphism Revealed by the Polymerase Chain Reaction," *Nucleic Acids Research*, 18(11) :3428, 1990.

Weisgraber, et al., "Apolipoproten C–I Modulates the Interaction of Apolipoprotein E With β–Migrating Very Low Density Lipoproteins (β–VLDL) and Inhibits Binding of β–VLDL to Low Density Lipoprotein Receptor–Related Protein," *Journal of Biological Chemistry*, 265(36) :22453–22459, Dec. 1990.

COMPOSITIONS AND METHODS FOR ASSESSING RISK FACTORS IN ALZHEIMER'S DISEASE

The present application claims priority to Provisional Application U.S. Serial No. 60/007,738, filed Nov. 29, 1995.

FIELD OF THE INVENTION

The present invention relates generally to compositions and methods for assessing risk factors in Alzheimer's disease. More particularly, it concerns compositions and methods relating to the detection of a particular allele, termed the APOCI allele, the presence of which has been found by the present inventors to be a risk factor for development of Alzheimer's disease. The invention also relates to methods for detecting the APOE4 allele in combination with the APOCI allele in improved screening techniques for monitoring the presence or the development of the disease. The nucleic acid probe molecules of the present invention provide superior methods for screening a sample for these alleles.

BACKGROUND OF THE INVENTION

Alzheimer's disease afflicts an estimated four million Americans and up to 600,000 cases of dementia are presented for diagnosis annually (Wall St. J., 1995). Patients with dementia must undergo a series of tests to eliminate other possible diseases to try to narrow the diagnosis to Alzheimer's. Such tests can take weeks and cost considerable sums of money. Although no effective treatment currently exists for most of these patients, quicker diagnosis of Alzheimer's will enable physicians and family members to properly care for patients.

The cause of Alzheimer's disease is not known. The disease is a genetically heterogeneous neurological disorder characterized by progressive dementia. Characteristic pathological features of Alzheimer's disease include the presence of senile plaques and neurofibrillary tangles (highly insoluble protein aggregates) throughout the brain, particularly in those regions involved with memory and cognition. The protein apolipoprotein E (APOE) has been found to be associated with the β amyloid protein found in both the plaques and tangles. The gene for APOE is found on chromosome 19q13.2; it is polymorphic, consisting of three alleles, E2, E3, and E4. Between 40–50% of late onset Alzheimer's patients have at least one copy of the APOE4 allele, and APOE4 has been identified as a risk factor for Alzheimer's disease (Saunders et al., 1993; Strittmatter et al., 1993).

U.S. Pat. No. 5,434,050 relates to detection and quantitation of amyloid deposition in a patient, while U.S. Pat. No. 5,441,870 relates to detection and monitoring of a secreted amino-terminal fragment of β-amyloid precursor protein, associated with Alzheimer's disease. PCT publication, WO 95/16791, the entire reference of which is incorporated by reference herein, relates to methods for the clinical determination of the risk of late-onset Alzheimer's disease or for the diagnosis or prognosis of Alzheimer's disease, the methods involving the determination of the number of copies of the APOE4 allele in a patient sample. WO 94/09155 relates to methods of diagnosing or prognosing Alzheimer's disease involving detecting the presence or absence of an apolipoprotein E type 4 isoform or DNA encoding APOE4 in a subject.

Apolipoprotein CI is a plasma protein of 6600 Da consisting of 57 amino acids (Shulman, et al., 1975). In the circulation, the Apo CI protein is associated with chylomicrons, as well as LDL and VLDL lipoproteins. The function of the protein is not understood, but it is known that it is produced primarily in the liver. Trace amounts are found in brain. Transgenic mice deficient in APOCI have an impaired receptor-mediated clearance of degraded lipoproteins. ApoCI has been reported to block ApoE-mediated uptake of β-VLDL by hepatic receptors (Weisgraber, et al., 1990; Sehayek, 1991).

The gene for APOCI is located on chromosome 19 (19q12–19q13.2) within a 45 kb cluster of apolipoprotein genes. Each lipoprotein gene consists of 4 exons and three introns, suggesting a common ancestral gene (Lauer, et al., 1988). Upstream from the APOCI gene is that for APOE, and downstream are a pseudogene APOCI', and the APOCIV, and APOCII genes. The gene for APOCI is 3' to that for APOE, with 5500 bp separating the two genes.

The APOCI gene has three known polymorphisms: a BglI site at position 673 (Accession M20902 Genbank), a DraI site, and an HpaI site at position 175 (Frossard, et al., 1987; Frossard, et al., 1987; Nillesen, et al., 1990). The primary transcript starts at position 493.

It has been suggested that the E4 allele of the APOE gene is in linkage disequilibrium with the CI HpaI site of the APOCI gene(Chartier-Harlin, 1994). However, the relationship of APOCI as a clinical risk factor for Alzheimer's disease has not been investigated.

Many factors affect the association of a disease with a particular allele. For example, the level of linkage disequilibrium between a mutation and a disease is determined by the time passed since the mutation and the recombination frequency. Forces such as selection, mutation, and/or migration can change gene frequencies over time. Population stratification can also have major effects. In the search for the Huntington's gene, significant differences were found with associations of particular markers and several distinct populations. For example, families from the UK showed significant association of the disease with the marker D4S95, while Danish families did not (Andrew, et al., 1993). In a more recent study of gene mapping in which Caucasian and Japanese families with Werner's syndrome were analyzed, it was found that 5 markers on chromosome 8 had evidence of linkage disequilibrium in Caucasian families. The Japanese families had evidence of linkage disequilibrium to 4 additional markers (Goddard, et al., 1966). This indicates that there are probably several mutations in the two populations. Ethnic specific allele frequencies, multiple origins of a mutation, and sample size can all have profound effects on allelic association. Hence, observation that particular alleles share a linkage disequilibrium alone is insufficient and at times is an erroneous basis to assess risk or presence of disease.

Since the cause of Alzheimer's disease is not known, the disease and predisposition to it are difficult to diagnose. The identification of additional risk factors may assist in both diagnosis of Alzheimer's disease and in designing future therapy and/or preventive measures for Alzheimer's disease. Because of all of the above problems, known procedures are not completely satisfactory, and persons skilled in the art have searched for improvements.

SUMMARY OF THE INVENTION

The present inventor has examined the frequency of the presence of the APOCI restriction site (AA) in Alzheimer's patients and in control spouses, and found a correlation to exist between the APOCI allele and the incidence of Alzheimer's disease. This risk factor, while distinct from the APOE4 allele, demonstrates a positive correlation with the disease at frequencies as high as reported for APOE4. As such, an alternative to screening for APOE4 is provided, as well as an accurate confirmatory screening approach where ambiguous results with APOE4 were observed.

Thus, the present invention provides a method of determining the presence of a genetic risk factor for having or developing Alzheimer's disease for a patient. The method comprises detecting the presence or absence of an APOCI allele in a patient sample, wherein the presence of the APOCI allele indicates an about 5-fold risk of having or developing Alzheimer's disease. A "patient" may be a person not previously diagnosed as having Alzheimer's disease, one who has been initially diagnosed as having Alzheimer's disease but where confirming information is desired, one who has dementia, or one who previously was normal but is now showing symptoms of dementia.

In one aspect of the invention, a method for screening a biological animal sample for a genetic factor correlated with Alzheimer's disease is provided, the presence of said genetic factor indicating the presence of Alzheimer's disease or an enhanced risk of developing Alzheimer disease. The method comprises screening nucleic acid from the biological sample for the presence of an APOC1 allele, wherein the presence of the APOCI allele identifies the presence of Alzheimer's disease or an enhanced risk of developing Alzheimer's disease in the animal.

The screening step may be carried out using a number of methods known to one of skill in this art upon reading this disclosure. A patient sample, such as blood, plasma, lymphocytes, skin biopsy, hair, autopsy tissue, cerebrospinal fluid (CSF), or the like, containing genomic DNA is collected.

The screening comprises amplifying genomic DNA encoding an APOC region from the biological sample using at least one pair of APOC region-specific oligonucleotide primers to provide amplified DNA of the APOC region, incubating the amplified DNA with a restriction enzyme capable of cleaving DNA at sites specific for the APOC 1 region to form a digest, and determining the size of DNA fragments in the digest, wherein the presence of a DNA fragment having a size differing from the size of a DNA fragment from a control sample lacking the APOCI allele indicates the presence of the genetic factor. In particular, the restriction enzyme is further defined as a HpaI restriction enzyme.

In another embodiment of the invention, the detecting comprises i) amplifying genomic DNA encoding an APOC region in the patient sample using APOC region-specific oligonucleotide primers, ii) incubating the amplified DNA with HpaI restriction enzyme for a time sufficient to allow cleavage, and iii) determining a size of resultant restriction fragments, wherein the size of each fragment is compared with appropriately sized markers. Amplification may be carried out using any suitable means; examples include, but are not limited to, polymerase chain reaction, ligase chain reaction, strand displacement amplification, transcription-based amplification, self-sustained sequence replication, the Qβ replicase system, nucleic acid sequence-based amplification, the repair chain reaction, and boomerang DNA amplification. WO 94/09155 is incorporated by reference herein for citing amplification method references. Polymerase chain reaction is a preferred amplification method.

In general, the amplification method involves the use of a pair of nucleic acid primers, one that hybridizes 5', and one that hybridizes 3' to the DNA area to be amplified (Saiki et al., 1988, U.S. Pat. No. 4,683,202, both references are incorporated by reference herein). The size of DNA to be amplified may be from about 100 base pairs to about 10,000 base pairs, although one of skill in this art would realize that an optimal size would be about 1,000 base pairs. Ideally, the amplified fragment contains known restriction sites. Use of primer sets designated by SEQ ID NOS:1 and 2, and SEQ ID NOS:3 and 4 results in an amplified fragment that contains the HpaI site. Preferred APOC region-specific oligonucleotide primers have nucleotide sequences as in SEQ ID NOS:1 and 2, or SEQ ID NOS:3 and 4. The set of primers designated by SEQ ID NOS:3 and 4 are believed by the present inventor to provide an optimal amplified DNA fragment.

Ligase chain reaction (LCR) is carried out as described in Weiss, for example (Weiss, 1991, which reference is specifically incorporated by reference herein in its entirety for this purpose).

A general method for preparing oligonucleotides as primers of various lengths and sequences is described by Caracciolo et al. (1989). In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to be coupled is reacted with the free hydroxyl of a growing nucleotide chain derivatized to a solid-support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base. Oligodeoxynucleotides or their phosphorothioate analogues may be synthesized using an Applied Biosystem 380B DNA synthesizer (Applied Biosystems, Inc., Foster City, Calif.).

In another aspect of the invention, the detecting comprises determining the nucleotide sequence of a DNA region in the patient sample possibly having the APOCI allele, wherein when the nucleotide sequence includes a HpaI nucleotide sequence, then the APOCI allele is present. The HpaI nucleotide sequence is 5' GTTAAC 3'. Nucleic acid sequence analysis may be carried out by manual or automated methods. Automated analysis is based on fluorescence detection of DNA fragments extended from fluorescent dye-linked primers by the dideoxy-chain terminator method of Sanger et al., (1977). An automated DNA sequencer may be from Applied Biosystems, (Foster City, Calif.) or from Pharmacia Corp. (Piscataway, N.J.), for example.

In a further aspect of the invention, the detecting comprises hybridizing an APOCI allele specific probe to the patient sample, wherein specific hybridization indicates the presence of the allele. An APOCI allele-specific probe is a nucleic acid sequence having perfect complementarity to the region of DNA suspected of containing the allele. The nucleotide sequence of a region that includes the gene encoding APOC is provided as SEQ ID NO:7 and is found in Lauer et al., (1988), which reference is incorporated by reference herein. A mismatch between the patient sample and a probe results in a duplex nucleic acid molecule having thermal instability. A matched duplex has thermal stability. For a probe of about 15–25 nucleotides, a guide for the melting temperature of a matched duplex is 4° for every GC base pair and 2° for every AT base pair. Control duplexes are run along with the clinical specimens to assess thermal stability. For these applications that require high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand.

In certain embodiments, it will be advantageous to employ nucleic acid probes or primers in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In some embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

Where the patient sample is found to be homozygous for the presence of the APOCI allele, then the risk factor is about 5-fold greater than for absence of the allele for developing or having Alzheimer's disease. Where the patient sample is heterozygous for the presence of the APOCI allele, then the risk factor is about 2-fold greater than for absence of the allele for having or developing the disease.

A further aspect of the present invention is the detection of both the APOCI allele and the step of detecting the presence of an APOE4 allele in a patient sample, wherein the presence of the APOCI and APOE4 alleles indicate an about 14-fold risk of having or developing Alzheimer's disease. Interestingly, the risk of developing the disease increases to about 16-fold if there is a family history. The risk may be the sum of the risks of having each allele, or may be the greater risk of the two, depending upon whether the mutations work together or independently. In this embodiment, the further step of detecting the APOE4 allele may include i) amplifying genomic DNA encoding an APOE region in the patient sample using at least one pair of APOE region-specific oligonucleotide primers, ii) incubating the amplified DNA with a restriction enzyme capable of cleaving DNA at sites specific for the APOE4 region to form a digest; and iii) determining the size of resultant restriction fragments, wherein the presence of a DNA fragment having a size differing from the size of a DNA fragment from a control sample lacking the APOE4 allele indicates the presence of the APOE4 allele. Preferably, HhaI is the restriction enzyme. One of skill in this art, in light of this disclosure, would realize that isoschizomers of HhaI could be used for the enzyme digest, for example, HinPI, CfoI, and Hin6I. Preferred APOE region-specific oligonucleotide primers have nucleotide sequences as in SEQ ID NOS:5 and 6. When these or substantially similar primers are used, then the presence of an about 70 base pair HhaI fragment indicates the presence of the APOE4 allele.

When both the APOCI and APOE4 alleles are present in a patient sample, and when the patient is male, then the risk is for an age of onset of Alzheimer's disease at about 60–64 years; and when the patient is female, then the risk is for an age of onset of the disease at about 65–69 years.

A preferred method of screening for a genetic factor for having or risk of developing Alzheimer's disease comprises the steps of i) amplifying genomic DNA encoding an APOC region in a patient sample using a first oligonucleotide primer having a nucleotide sequence as in SEQ ID NO:1 and a second oligonucleotide primer having a nucleotide sequence as in SEQ ID NO:2, ii) incubating the amplified DNA with HpaI restriction enzyme for a time sufficient to allow cleavage, and iii) determining a size of resultant restriction fragments. The presence of a restriction fragment having a size of about 220 base pairs identifies a patient sample negative for the APOCI allele and without risk for developing Alzheimer's disease. The presence of a restriction fragment having a size of about 160 base pairs and a restriction fragment of about 60 base pairs identifies a homozygous APOCI allele profile and a 21-fold enhanced risk of having or developing Alzheimer's disease. The presence of a restriction fragment having a size of about 220, a restriction fragment having a size of about 160 base pairs, and a restriction fragment having a size of about 60 base pairs identifies a heterozygous APOCI allele profile and a 3-fold enhanced risk of having or developing Alzheimer's disease.

The above-described method may further comprise the steps of i) amplifying genomic DNA encoding an APOE region in the patient sample using at least one pair of APOE region-specific oligonucleotide primers, ii) incubating the amplified DNA with HhaI restriction enzyme, or isoschizomer thereof, for a time sufficient to allow cleavage, and vi) determining the size of resultant restriction fragments. When the size of a resultant restriction fragment is about 70 base pairs, then the patient has an about 35-fold enhanced risk of having or developing Alzheimer's disease.

Another aspect of the invention is a method of screening for a genetic factor for having or risk of developing Alzheimer's disease. The method comprises i) amplifying genomic DNA encoding an APOC region in a patient sample using a first oligonucleotide primer having a nucleotide sequence as in SEQ ID NO:3 and a second oligonucleotide primer having a nucleotide sequence as in SEQ ID NO:4, ii) incubating the amplified DNA with HpaI restriction enzyme for a time sufficient to allow cleavage, and iii) determining a size of resultant restriction fragments. The presence of a restriction fragment having a size of about 270 base pairs identifies a patient sample negative for the APOCI allele and without risk for developing Alzheimer's disease. The presence of a restriction fragment having a size of about 154 base pairs and a restriction fragment of about 95 base pairs identifies a homozygous APOCI allele profile and a 5-fold enhanced risk of having or developing Alzheimer's disease. The presence of a restriction fragment having a size of about 270 base pairs, a restriction fragment having a size of about 154 base pairs, and a restriction fragment having a size of about 95 base pairs identifies a heterozygous APOCI allele profile and a 2-fold enhanced risk of having or developing Alzheimer's disease.

The above-described method may further comprise the steps of i) amplifying genomic DNA encoding an APOE region in the patient sample using at least one pair of APOE region-specific oligonucleotide primers, ii) incubating the amplified DNA with HhaI restriction enzyme, or isoschizomer thereof, for a time sufficient to allow cleavage; and iii) determining the size of resultant restriction fragments, wherein when the size of a resultant restriction fragment is about 70 base pairs, then the patient has an about 14-fold enhanced risk of having or developing Alzheimer's disease.

Another embodiment of the invention is a method of screening a biological sample for a pathology correlated with a genetic factor located within the APOCI allele. The method comprises i) amplifying genomic DNA encoding an APOC region from the biological sample using at least one pair of APOC region-specific oligonucleotide primers to provide amplified DNA of the APOC region; ii) incubating the amplified DNA with a restriction enzyme capable of cleaving DNA sites specific for the APOCI region to form a digest; and iii) determining a size of DNA fragments in the digest, wherein the presence of a restriction fragment having a size differing from the size of a DNA fragment from a control sample lacking the APOCI allele indicates the presence of the pathology correlated with the genetic factor located within the APOCI allele.

The present invention also provides for an oligonucleotide having a sequence as defined in SEQ ID NO:1, SEQ ID NO:2, SEQ ID NO:3, SEQ ID NO:4, SEQ ID NO:5, or SEQ ID NO:6.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
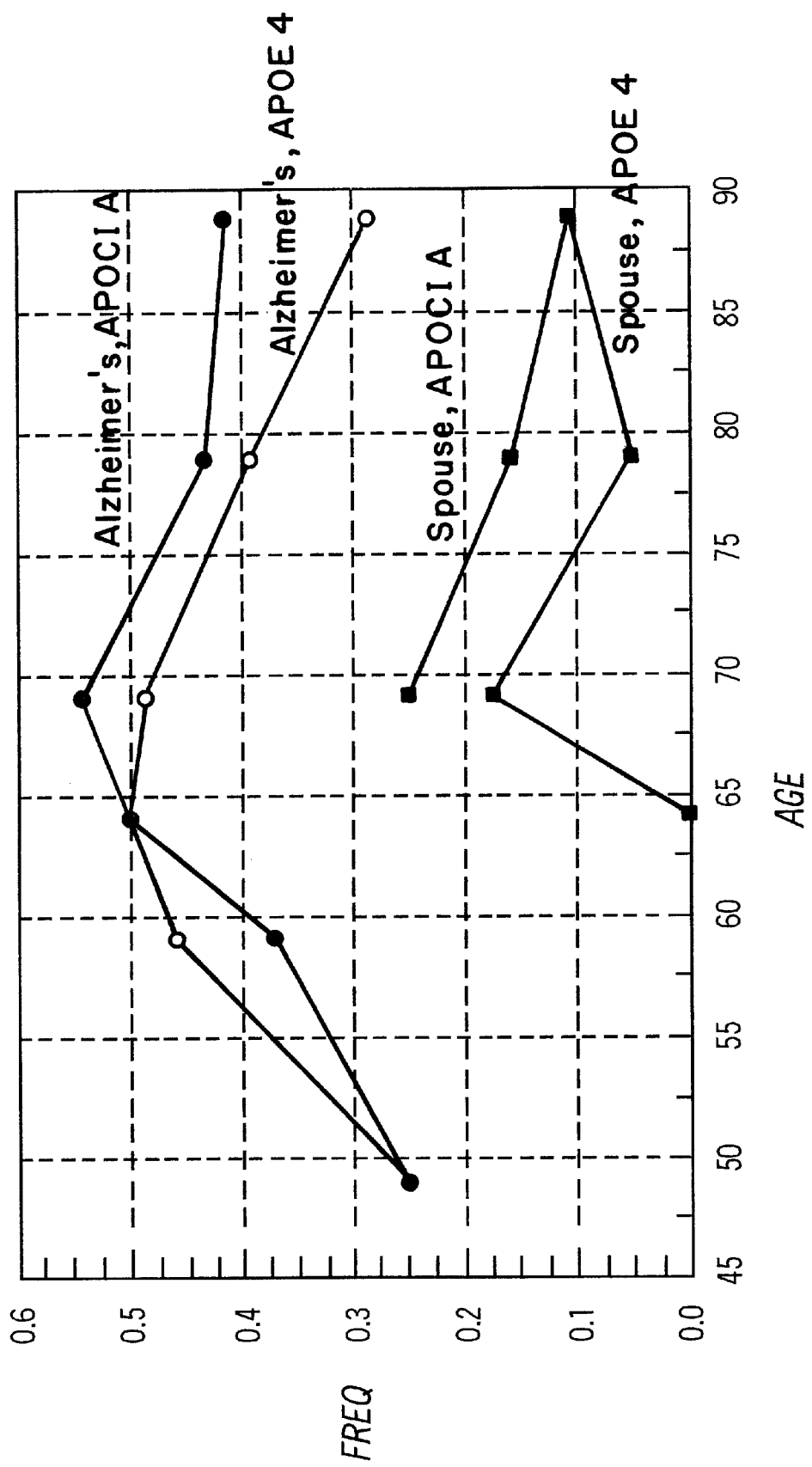
FIG. 1 shows APOCI A and APOE 4 allele frequencies vs. age of onset in Alzheimer's patients and ages of spouses.

An embodiment of the present invention is the detection of the APOCI allele as a significant risk factor for Alzheimer's disease. The frequency of the APOCI A allele is similar to that of the APOE 4 allele. In the present studies, the overall frequency of the APOCI allele in Alzheimer's patients was 0.448 compared with control samples which had a frequency of 0.161 of the APOCI allele. The frequency for APOE 4 in Alzheimer's patients was 0.411 compared with the frequency in control samples of 0.081.

No differences were found in the frequencies of either the APOCI allele or the APOE 4 allele in male vs. female patients but significantly lower frequencies were found in sporadic vs. familial Alzheimer's patients. The average age of onset of symptoms was 67–68 years for both the APOCI A and APOE 4 alleles. Male patients have an earlier age of onset (60–64 years) than females (65–69 years) when the frequencies of both alleles were examined.

Other markers and genes surrounding APOE on chromosome 19 were examined for additional associations with Alzheimer's disease. No associations were found with the BCL3 or the LIPE genes or with the marker D19S47; and only very weak associations were found with APOCII.

For this study, the diagnosis of probable Alzheimer's disease was confirmed on 250 patients using criteria for diagnosis according to NINCDS-ADRDA (McKhann, et al., 1984). These criteria included a detailed medical history, appropriate blood work to rule out factors such as vitamin B12 or thyroid deficiency, and evidence of cerebral atrophy on CAT scans or MRIs. The medical history documented the progressive nature of the illness and ruled out cardiovascular problems. Those with possible Alzheimer's disease or with vascular dementia were excluded from the study. Autopsy confirmations of the diagnosis on 50 patients have been obtained.

For this study, the probable Alzheimer's patients consisted of 59 with early onset disease (before the age of 65) and 151 with late onset disease. The patients were of European descent who migrated to Texas; they were non-Hispanic, non-Black, and non-Indian. Spouses (289 in number) of similar ethnic background and environmental exposure were used as controls (average age 72.4±8.24).

Twenty extended Alzheimer's families with multiple affecteds (total sample size of affecteds and unaffecteds-268) were assessed for both the APOCI and APOE alleles. In addition, CEPH families with an APOE4 allele were analyzed for the presence of the APOCI restriction site. Patients from the Indiana University Alzheimer's Disease National Cell Bank were evaluated for both the APOE4 allele and the APOCI restriction site. DNA samples from 17 late onset families with at least two affected siblings were obtained from the NIMH Alzheimer's disease genetics initiative cell repository and were analyzed for the APOCI A allele and the APOE 4 allele.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Methods for Determining Presence of APOCI Allele

The present example provides methods for determining the presence or absence of the APOCI allele in a patient sample. Genomic DNA extracted from blood or transformed lymphocytes was used for this study, although samples may be obtained from other bodily tissues as known to one of skill in the art in light of the present disclosure. DNA was extracted by a modification of the procedure of Grimberg et al. (1989). For this procedure, 2 mL of blood was diluted with one volume of PBS, mixed and centrifuged. The pellet was resuspended twice in 1.5 mL of CLB (0.32M sucrose, 10 mM Tris-HCl, pH 7.6, 5mM $MgCl_2$, 1% Triton X-100) with mixing and centrifugation each time. The pellet was then suspended in 0.5 mL of PLB (10 mM Tris-HCL, pH 8.0, 10 mM NaCl, 10 mM EDTA) containing 1 mg/mL of proteinase K and incubated at 65° C. for two hours, with occasional shaking. This was followed by three buffered phenol extractions and one chloroform extraction. The DNA was precipitated with 0.2 volume of 10 M ammonium acetate and 2 volumes of ethanol. After centrifugation, the DNA pellet was dried and resuspended in 100 µl of TE. For PCR reactions, a 1:100 dilution of DNA was used.

The primers used to amplify the HpaI restriction site were as described by Nillesen et al. (1990); which is specfically incorporated herein by reference for this purpose. The 5' primer is located at position 113 in the Genbank sequence (Accession Number M20902) which is at position –380 bp from the primary transcript start site at position 493. Primers were from Midland Certified Reagents Co. (Midland, Tex.).

The 5' primer is GAG CTC GGC TCT TGA GAC AGG AA, SEQ ID NO:1.

The 3' primer is GGT CCC GGG CAC TTC CCT TAG CCC CA, SEQ ID NO:2.

The 3' primer is located at position 335 which is −158 from the start site. The polymorphic HpaI restriction site is at position 175.

The PCR reaction consisted of 2.5 µl Thermo DNA polymerase 10× reaction buffer 2.5 µl 200 µM dNTP 1 µl each primer (1 O.D. unit/ml or 20 pmol)

1.2 µl 25 mM $MgCl_2$ 0.2 µl 5000 Units/ml Taq polymerase 15.6 µl $H_2O$

To this was added 1 µl of genomic DNA (100–200 ng).

The DNA was amplified for 30 cycles with the following program: 95° C. for 10 min; then 30 cycles of 95° C. for 50 sec, 58° C. for 50 sec, or 72° C. for 90 sec, then a final extension at 72° C. for 10 min.

The restriction digestion consisted of

1 µl of 10× buffer #4 (New England Biolab)

1 µl 5000 Units/ml HpaI

3 µl $H_2O$

To this was added 5 µl of the PCR product which was incubated at 37° C. for 16 hours.

The digested samples were subjected to electrophoresis on a 5% polyacrylamide gel in TBE run at 75 volts until the marking dye was at the bottom (approximately 3 hours). After ethidium bromide staining, bands of 222, 160, and 62 bp were evident. The samples that lacked the HpaI restriction site had a fragment size of 222 bp (BB). Samples with the restriction site present had the fragment sizes of 160 and 62 bp (AA). Those who were heterozygous had all three bands present (AB).

A further set of primers are used in some embodiments for amplification of the fragment surrounding the HpaI site, i.e., the APOCI allele. The 5' and 3' primers are:

5' CAT CCC CTG CTT GTT CAA TCG, SEQ ID NO:3

5' CAC TCT CAC CTC TCA ATC TTC C, SEQ ID NO:4

The size of the amplified fragment using this set of primers is about 270 bp. Therefore, the sizes of the fragments after restriction enzyme digestion with HpaI are about 154 and about 95 bp if the APOCI allele is present and the patient is homozygous, the size is about 270 bp if the allele is absent and the patient is homozygous, and fragments of about 270, 154, and 95 bp are present if the patient is heterozygous for the allele.

The primer as set forth in SEQ ID NO:3 has no homology with sequences in the 5' region of an APOCI pseudogene located downstream from APOCI, whereas the primer sequence as set forth in SEQ ID NO:1 is highly homologous. Thus, the primer having a sequence as set forth in SEQ ID NO:3 will bind specifically to only one site on a template, whereas the primer having a sequence as set forth in SEQ ID NO:1 will bind to more than one site; the fragment amplified using primers 3 and 4 are more specific and provide cleaner results for the analysis of APOCI.

EXAMPLE 2

Methods for Determining Presence of APOE Alleles

The present example provides methods for determining the presence or absence of the APOE allele in a patient sample. Genomic DNA was prepared as described in example 1.

Primers used for restriction isotyping of APOE were as described by Hixson and Vernier (1990). Hixson and Vernier (1990) is specifically incorporated herein by reference for his purpose. The primers were 5' ACA GAA TTC GCC CCG GCC TGG TAC AC, SEQ ID NO:5, and 5' TAA GCT TGG CAC GGC TGT CCA AGG A, SEQ ID NO:6.

The PCR reaction consisted of 2.5 µl 10× reaction buffer 2.5 µl 200 µM dNTP 2.5 µl DMSO 1.0 µl each primer (20 pmol)

1.5 µl 25 mM $MgCl_2$ 0.2 µl 5000 Units/ml Taq polymerase 12.8 µl $H_2O$

To this was added 1 µl (100–200 ng) of genomic DNA. The DNA was amplified for 40 cycles with the following program: 94° C. for 10 min, then 40 cycles of 94° C. for 1 min, 65° C. for 1 min, 72° C. for 2 min, then a final extension at 72° C. for 10 min.

The restriction digestion consisted of 1.0 µl 10× buffer #4 (New England Biolab)

0.25 µl 20,000 Units/ml HhaI 0.05 µl 100 µg/ml BSA 3.7 µl $H_2O$

To this was added 5 µl of the PCR product which was then incubated at 37° C. for 16 hours.

The digested samples were subjected to electrophoresis on a 7.5% polyacrylamide gel in TBE run at 75 volts until the marking dye reached the bottom (approximately three hours). After staining with ethidium bromide, genotypes were scored by the presence of the upper three bands, a 91 bp fragment for APOE3, an 83 bp fragment for APOE2, and a 72 bp fragment for APOE4.

Allele frequencies were done by counting alleles and calculating sample proportions. Chi square analysis was done using the Statistica Software (Tulsa, Okla.). Relative risk was calculated as described by Elston and Johnson (1994). Haplotype frequencies were computed using the EH program (Terwilliger and Ott, 1994). The frequency used for the disease gene was 0.038, assuming that the disease was autosomal dominant with a penetrance of 0.83 after age adjustment (Farrer and Cupples, 1994).

EXAMPLE 3

Screening for APOCI Provides Nonambiguous Results Compared to Results from APOE4 Screening The present example provides a study where analysis of the APOE genotypes in Alzheimer's patients was ambiguous. In contrast, analysis of the APOCI genotype clearly demonstrated the probable APOE genotype.

Figure 4:
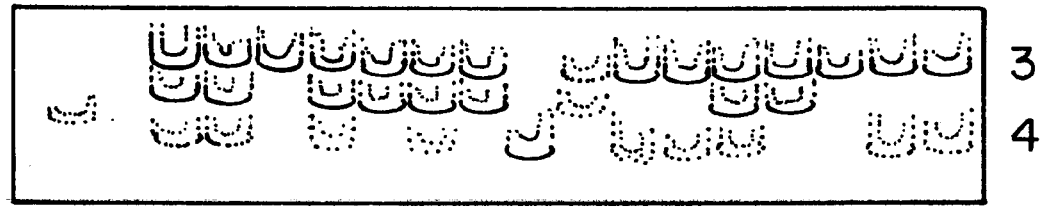
FIG. 4 shows a photograph of an ethidium bromide stained gel of Alzheimer's patients' DNA samples which have been amplified with the APOE primers and digested with HhaI.
Figure 5:
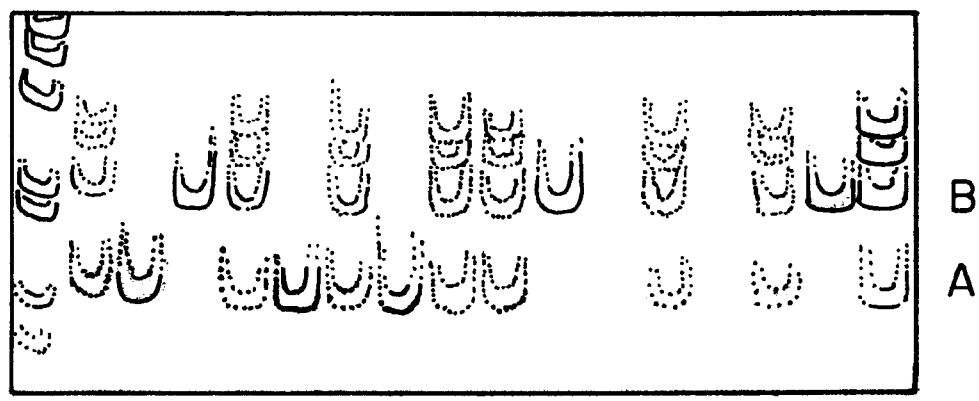
FIG. 5 shows a photograph of an ethidium bromide stained gel of DNA samples which have been amplified with the APOCI primers and digested with HpaI.

FIG. 4 shows a photograph of an ethidium bromide stained gel of Alzheimer's patients DNA samples which have been amplified with the APOE primers and digested with HhaI; the phenotype of sample 134012 can either be APOE 3/3 or 3/4. FIG. 5 shows a photograph of an ethidium bromide stained gel of DNA samples which have been amplified with the APOCI primers and digested with HpaI. Here, the data of sample 134012 indicate the APOCI AB allele, which strongly suggests that the APOE phenotype was APOE 3/4. This is demonstrated in the following examples.

EXAMPLE 4

Correlation of APOE Genotype with that of APOCI

The present example provides data that show a correlation of the APOE genotype with the genotype of the APOCI allele in patients. Of 105 probable Alzheimer's patients who were heterozygous for the APOE4 allele (3/4), 99 were also heterozygous for the APOCI restriction site (AB) as shown in Table 1. There were 32 probable Alzheimer's patients who were homozygous for the APOE4 allele (4/4) and 29 of these were homozygous for the presence of the APOCI restriction site (AA). Some 56 of the 61 patients homozygous for the APOE3 allele (3/3) lacked the APOCI restriction site (BB). These data demonstrate that the APOE4 allele and the presence of the APOCI HpaI restriction site were closely linked.

TABLE 1

Correlation of APOE Genotype with that of APOCI

| | APOE | | APOCI | | |
|---|---|---|---|---|---|
| | Genotype | Number | Genotype* | Number | % |
| pAD | 3/4 | 105 | AB | 99 | 94 |
| Spouses | 3/4 | 13 | AB | 8 | 62 |
| Linkage Families | 3/4 | 97 | AB | 96 | 99 |
| CEPH | 3/4 | 27 | AB | 26 | 96 |
| Indiana AD | 3/4 | 20 | AB | 20 | 100 |
| pAD | 4/4 | 32 | AA | 29 | 91 |
| Spouses | 4/4 | 0 | AA | 0 | — |
| Linkage Families | 4/4 | 20 | AA | 20 | 100 |
| CEPH | 4/4 | 8 | AA | 7 | 88 |
| Indiana AD | 4/4 | 3 | AA | 2 | 67 |
| pAD | 3/3 | 61 | BB | 56 | 92 |
| Spouses | 3/3 | 65 | BB | 52 | 80 |

TABLE 1-continued

Correlation of APOE Genotype with that of APOCI

| | APOE | | APOCI | | |
|---|---|---|---|---|---|
| | Genotype | Number | Genotype* | Number | % |
| Linkage Families | 3/3 | 126 | BB | 124 | 98 |
| CEPH | 3/3 | 72 | BB | 72 | 100 |
| Indiana AD | 3/3 | 5 | BB | 5 | 100 |

*A denotes restriction site present; B, absent.
% Refers to the % of the APOCI genotype compared with the APOE genotype. The various groups are as described in the Methodology section.

Initially,
none of the spouses were homozygous for the APOE4 allele (4/4), therefore, other DNA banks and linkage families were screened for those who were. In 20 extended linkage families, there were 20 Alzheimer's patients who were homozygous for the APOE4 allele. All of them had the APOCI HpaI restriction site (AA). Seven out of 8 CEPH families having the APOE 4/4 phenotype were APOCI AA (had the HpaI restriction site present). Interestingly, 100% of the CEPH families who were of the APOE 3/3 genotype were APOCI BB (lacked the restriction site). Of the probable Alzheimer's patients' DNA obtained from the Indiana cell bank, 20 of the patients were heterozygous for the APOE4 allele (3/4) and were also heterozygous for the APOCI restriction site (AB).

The
frequencies of the two polymorphisms in these groups are shown in Table 2.

TABLE 2

Frequencies of the APOCI and APOE Genotypes

| | pAD | Spouses | Linkage Families | CEPH | Indiana |
|---|---|---|---|---|---|
| APOCI | | | | | |
| Allele A | 0.448* | 0.161* | 0.340 | 0.293 | 0.431 |
| Allele B | 0.552* | 0.839* | 0.660 | 0.707 | 0.569 |
| APOE | | | | | |
| Allele 2 | 0.026 | 0.081 | 0.061 | 0.131 | — |
| Allele 3 | 0.562* | 0.839* | 0.671 | 0.714 | 0.536 |
| Allele 4 | 0.411* | 0.081* | 0.267 | 0.155 | 0.464 |

*Chi square analysis revealed significant differences between the pAD and spouses with p = 0.000 at df = 1.

The frequency for the presence of the APOCI HpaI restriction site in Alzheimer's patients was 0.448, in the Alzheimer's patients from the Indiana DNA bank was 0.431, and in the control spouses was 0.161. Chi square analyses of patients compared with controls (spouses) gave highly significant results (p=0.000 for the A allele and p=0.000 for the B allele at df=1). The frequency of the APOCI A allele in the patients (0.448) was similar to the frequency of the APOE4 allele (0.411). The DNA from 71 Alzheimer's patients in the 17 families was also analyzed. The frequency for the APOCI A allele was 0.472 and for the APOE 4 allele was 0.458. The analysis of 4 different sets of Alzheimer's patiens and two sets of controls provided consistent results. The frequency for the APOCI A allele in Alzheimer's patients was 40–50% and in control spouses was less than half of that.

The
frequency of the presence of the HpaI restriction site (AA) located in the 5' end of the APOCI gene is also very high in Alzheimer's patients. In analyzing 210 Alzheimer's patients and 94 spouses, it was found that 45% of the Alzheimer's patients have the restriction site present while only 16% of the control spouses have the site. Members of the CEPH DNA bank as well as patients from the Indiana University Alzheimer's disease National Cell Bank were examined for both the APOCI restriction site and the APOE4 allele. Of the Ceph family members who were homozygous for the APOE4 allele, 88% were also homozygous (AA) for the presence of the APOCI restriction site. With the Indiana Alzheimer's patients, most were heterozygous for the APOE4 allele. Of this group, 100% were also heterozygous (AB) for the presence of the APOCI restriction site.

The DNA from 71 Alzheimer's patients in the 17 families obtained from the NIMH was also analyzed. The frequency of the APOCI A allele was 0.472 and for the APOE 4 allele was 0.458. Thus analyzing 4 different sets of Alzheimer's patients and two sets of controls provide consistent results. The frequency for the APOCI A allele in Alzheimer's patients is 40–50% and in control spouses is less than half of that.

EXAMPLE 5

Frequencies of APOE and APOCI Genotypes in Male vs. Female and in Familial vs. Sporadic Patients The present example provides data showing the frequencies for the two polymorphisms in both male and female patients. The data are presented in Table 3.

TABLE 3

Frequencies of the APOCI and APOE Genotypes in Male vs Female Alzheimer's Patients

|  | Males | Females |
|---|---|---|
| APOCI |  |  |
| Allele A | 0.441 | 0.446 |
| Allele B | 0.559 | 0.554 |
| APOE |  |  |
| Allele 2 | 0.022 | 0.029 |
| Allele 3 | 0.581 | 0.554 |
| Allele 4 | 0.397 | 0.417 |

Some 72 males and 143 females were evaluated. The data show that there were no differences in frequencies for either the APOCI or the APOE polymorphisms between male and female patients. The average age of onset for these polymorphisms in male and female patients were also examined. The average age for the APOCI AA phenotype in males was 67±6.28 and in females was 69.7±7.90 years; for the AB phenotype in males was 69.7±7.36 and in females was 71.19±8.37. The average age for the APOE 4/4 phenotype in males was 65.2±5.96 and in females was 67.18±7.6 years; for the 3/4 phenotype was 69.58±7.08 in males and 70.5±8.36 years in females. There were no significant differences between males vs females in the average age of onset in these studies.

The frequencies for sporadic patients vs those with a family history of the disease are in Table 4.

TABLE 4

Frequencies of the APOCI and APOE Genotypes in Familial vs Sporadic Alzheimer's Patients

|  | Familial | Sporadic |
|---|---|---|
| APOCI |  |  |
| Allele A | 0.496* | 0.389* |
| Allele B | 0.504 | 0.611 |
| APOE |  |  |
| Allele 2 | 0.018 | 0.038 |
| Allele 3 | 0.518 | 0.623 |
| Allele 4 | 0.464 | 0.340 |

*Chi square analysis revealed significant differences between the familial and sporadic patients with p = 0.0000 at df = 1.

Some 115 patients with a family history and 55 sporadic patients were evaluated. The sporadic patients had slightly lower frequencies for both polymorphisms, which were significant (p=0.0000 at df=1).

EXAMPLE 6

Frequencies of APOE and APOCI Genotypes With Age

The present example provides data demonstrating the frequencies for the two polymorphisms with age in patients and controls. The average age of onset was examined for the APOCI and APOE genotypes in all of the Alzheimer's patients. The data are shown in Table 5.

The onset age for the APOCI AA phenotype was about 69 years; that for the AB and BB phenotypes were 69–70 years of age. No differences in age of onset with the APOE 4/4, 3/4, 3/3 phenotypes were noted (67–70 years). There was a possibility that the APOE 2/3 and 2/4 phenotypes had a slight delay in onset, 75–79 years; however, the number of patients having the E2 allele were quite small. If only familial patients were analyzed, no differences were found in the age of onset with either the APOCI or the APOE genotypes, regardless of whether all familial cases or only cases with age of onset after 60 years were analyzed.

TABLE 5

Average Age of Onset for APOCI and APOE Genotypes in Alzheimer's Patients

|  | Total | | Familial | | Familial-over 60 years of age | |
|---|---|---|---|---|---|---|
|  | Number | Age | Number | Age | Number | Age |
| APOCI |  |  |  |  |  |  |
| AA | 39 | 68.79 ± 7.43 | 25 | 68.36 ± 6.65 | 23 | 69.39 ± 5.84 |
| AB | 110 | 70.80 ± 8.03 | 61 | 70.61 ± 8.77 | 55 | 72.51 ± 6.78 |

TABLE 5-continued

Average Age of Onset for APOCI and APOE Genotypes in Alzheimer's Patients

|  | Total | | Familial | | Familial-over 60 years of age | |
|---|---|---|---|---|---|---|
|  | Number | Age | Number | Age | Number | Age |
| BB | 61 | 69.11 ± 10.04 | 26 | 67.92 ± 11.19 | 19 | 73.89 ± 4.85 |
| APOE | | | | | | |
| 4/4 | 32 | 66.56 ± 7.09 | 22 | 67.00 ± 6.45 | 19 | 68.68 ± 5.13 |
| 3/4 | 105 | 70.40 ± 8.03 | 58 | 70.45 ± 8.90 | 52 | 72.38 ± 6.99 |
| 2/4 | 3 | 76.67 ± 3.06 | 2 | 78.00 ± 2.80 | 2 | 78.00 ± 2.80 |
| 3/3 | 61 | 69.90 ± 9.49 | 28 | 68.25 ± 10.65 | 22 | 73.09 ± 5.03 |
| 2/3 | 8 | 74.50 ± 11.70 | 2 | 77.50 ± 3.50 | 2 | 77.50 ± 3.50 |

TABLE 6

Frequencies of the APOCI and APOE Genotypes with Age in Alzheimer's patient and Control Spouses

| | APOCI | | | | | APOE | | | | | |
|---|---|---|---|---|---|---|---|---|---|---|---|
| | Allele B | | Allele A | | | Allele 4 | | Allele 3 | | Allele 2 | |
| Age | AD | Spouses | AD | Spouses | | AD | Spouses | AD | Spouses | AD | Spouses |
| <50 | 0.750 | — | 0.250 | — | | 0.250 | — | 0.750 | — | — | — |
| 50–59 | 0.630 | — | 0.370 | — | 0.457 | — | 0.522 | — | 0.022 | — | |
| 60–64 | 0.500 | 1.000 | 0.500 | — | 0.500 | — | 0.500 | 1.000 | — | — | |
| 65–69 | 0.457 | 0.750 | 0.543 | 0.250 | 0.486 | 0.175 | 0.486 | 0.775 | 0.029 | 0.050 | |
| 70–79 | 0.566 | 0.840 | 0.434 | 0.160 | 0.394 | 0.053 | 0.591 | 0.830 | 0.015 | 0.117 | |
| >80 | | 0.583 | 0.889 | 0.417 | 0.111 | 0.292 | 0.111 | 0.625 | 0.889 | 0.083 | — |

The frequencies of the APOCI and APOE genotypes were correlated with the age of onset in both Alzheimer's patients and control spouses as shown in Table 6. There was an apparent increase in the frequency of the APOCI A allele with age of onset, with the highest frequency occurring at ages 65–69 years (frequency 0.543). The highest frequency for the APOE 4 allele may be slightly earlier, at ages 60–64 years; however, the difference in frequencies between 60–64 years and 65–69 years are slight and not significant (0.500 vs 0.486, respectively). FIG. 1 demonstrates this trend. Since there were few spouses under the age of 65 years, the frequencies of the APOCI and APOE genotypes in spouses over the age of 65 years were examined. There was an apparent decrease in the frequencies of both the APOCI A allele and the APOE 4 allele as the spouses entered their seventh decade of life.

Figure 2:
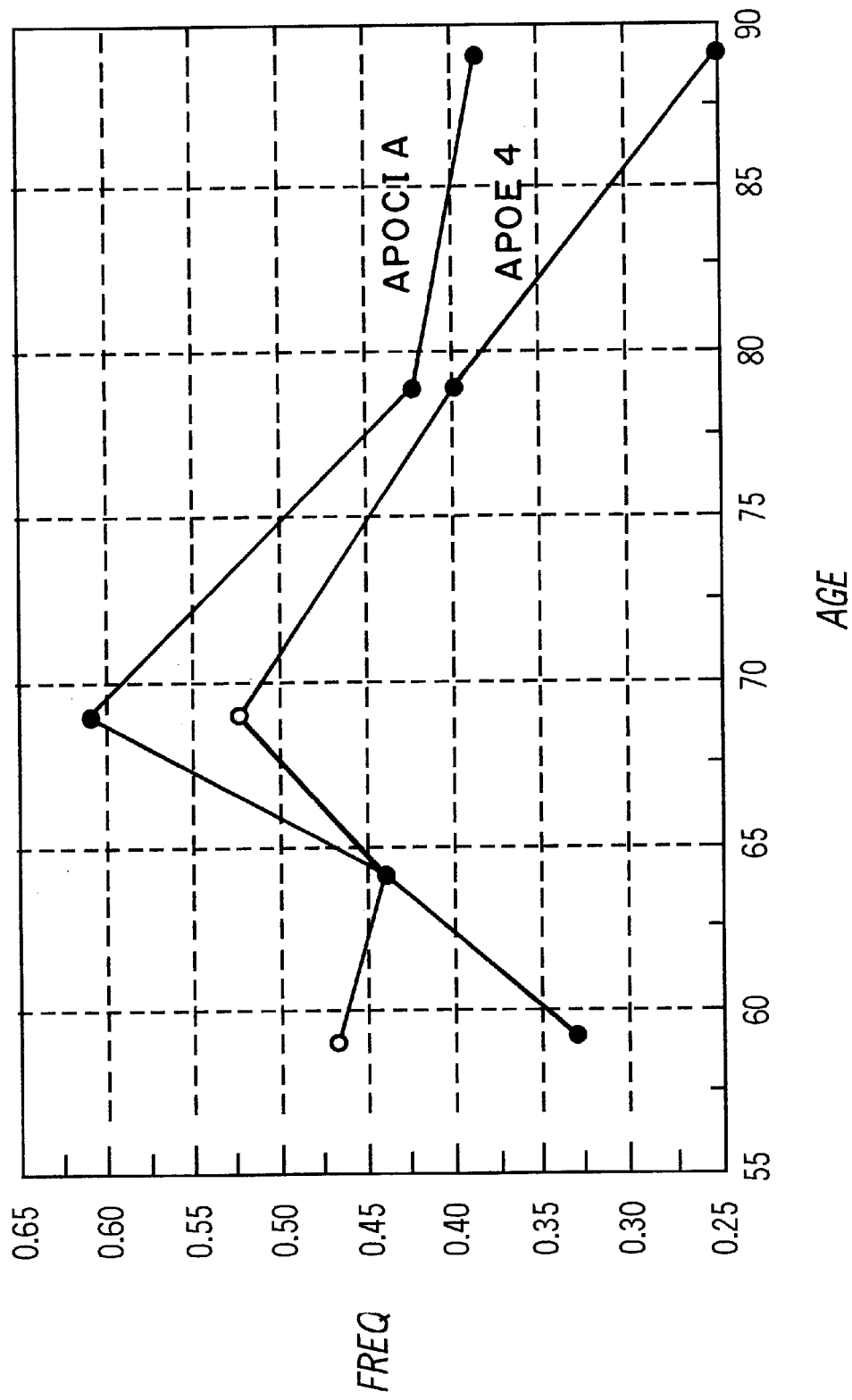
FIG. 2 shows APOCI A and APOE 4 allele frequencies vs. age of onset in female Alzheimer's patients.
Figure 3:
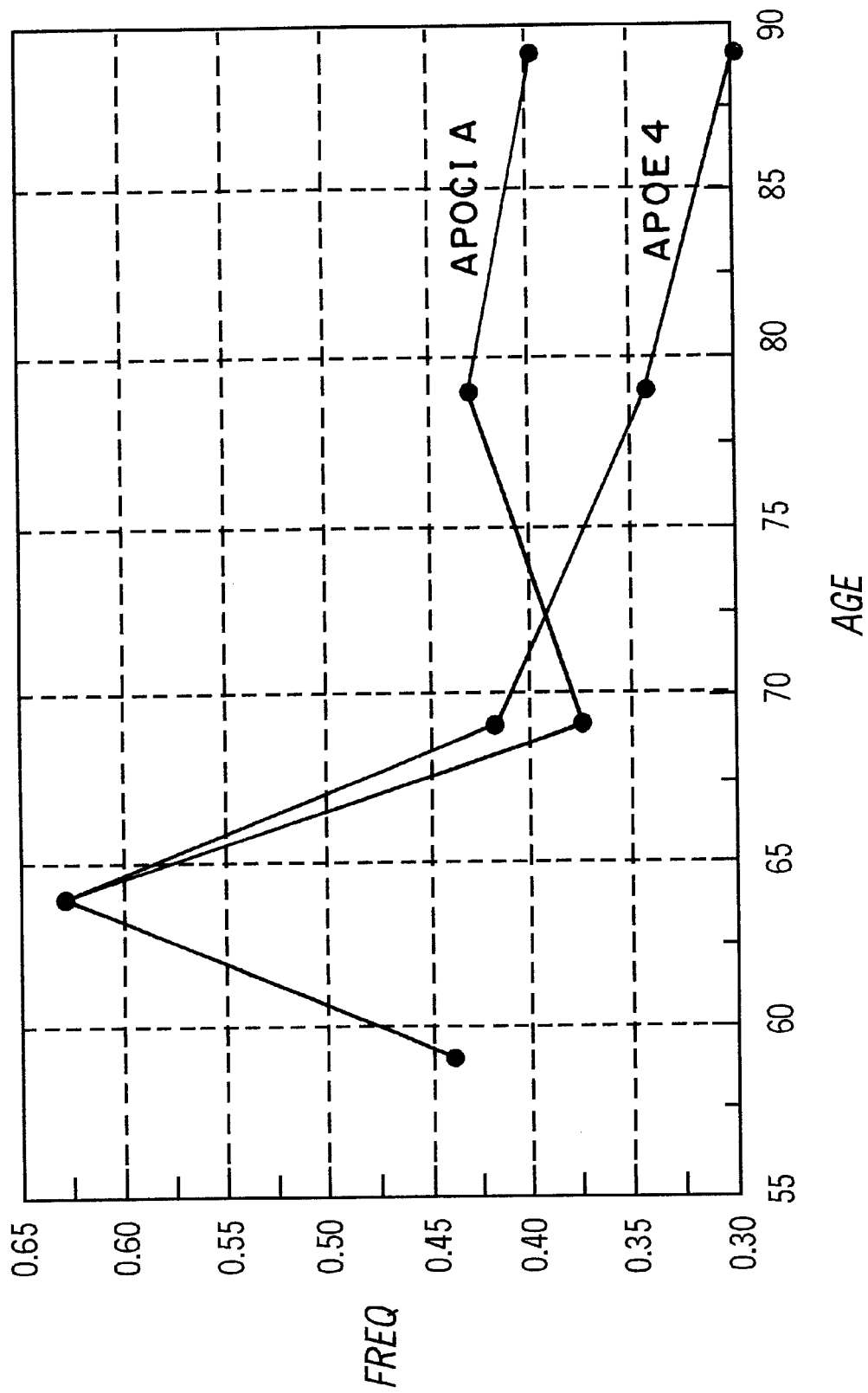
FIG. 3 shows APOCI A and APOE 4 allele frequencies vs. age of onset in male Alzheimer's patients.

When the frequencies of the APOCI A allele and the APOE 4 allele are graphed vs age of onset for the male vs female Alzheimer's patients, differences were noted as shown in FIG. 2 and FIG. 3. Male patients had an earlier age of onset (60–64 years) than females (65–69 years) when the frequencies of either the APOCI A allele or the APOE 4 allele were evaluated. These differences are highly significant with p=0.0000 at df=1.

EXAMPLE 7

Odds Ratios for Alzheimer's Patients vs. Controls

The present example provides the odds ratios for Alzheimer's patients vs control spouses. The data are presented in Table 7.

TABLE 7

Odds Ratios for Alzheimer's Patients vs Control Spouses

| | Total | Male | | Familial | | Sporadic | |
|---|---|---|---|---|---|---|---|
| | pAD | pAD | Female pAD | Male | Female | Male | Female |
| APOCI | | | | | | | |
| AA | 4.8 | 4.0– | 5.6– | 5.1 | 5.4 | — | 5.4 |
| AB | 2.0 | 2.1 | 2.0 | 1.8 | 1.9 | 3.6 | 2.2 |
| APOE | | | | | | | |
| 4/4 | 8.7 | 7.5* | 9.8* | 10.5 | 10.9 | — | 6.8 |
| 3/4 | 4.0 | 4.7 | 3.7 | 4.7 | 3.4 | 4.8 | 4.5 |

$-X^2 = 5.13$, p = 0.0235 at 1 df
$*X^2 = 22.65$, p = 0.0000 at 1 df

The studies of spouse controls were extended to include 245 samples. These 245 samples were made up of 101 males and 144 females. Of these samples, 6 were found to have the APOCI AA/APOE 4/4 genotype (3 male and 3 females). The results of the odds ratio study indicate that the risk of developing the disease was 5× greater for individuals having the APOCI AA phenotype than for those having the APOCI BB phenotype.

The risk of developing the disease was 9× greater with the APOE 4/4 genotype. Females were at a somewhat higher risk than males. Heterozygotes were at considerably lower risk for developing the disease.

TABLE 8

Haplotype Frequencies of APOCI, APOE, and Alzheimer's Disease

| Disease Allele | APOE Allele | APOCI Allele | Haplotype Frequency Independent | Independent of Disease | Associated With Disease |
|---|---|---|---|---|---|
| — | 2 | A | 0.030158 | 0.025837 | 0.036729 |
| — | 2 | B | 0.077840 | 0.082161 | 0.123252 |
| — | 3 | A | 0.154845 | 0.027004 | 0.037440 |
| — | 3 | B | 0.399667 | 0.527507 | 0.639106 |
| — | 4 | A | 0.083631 | 0.215793 | 0.115570 |
| — | 4 | B | 0.215859 | 0.083697 | 0.009903 |
| D | 2 | A | 0.001191 | 0.001021 | 0.000158 |
| D | 2 | B | 0.003075 | 0.003245 | 0.000000 |
| D | 3 | A | 0.006117 | 0.001067 | 0.000317 |
| D | 3 | B | 0.015787 | 0.020837 | 0.011944 |
| D | 4 | A | 0.003304 | 0.008524 | 0.016370 |
| D | 4 | B | 0.008527 | 0.003306 | 0.009211 |

| | | df | Ln(L) | Chi-square |
|---|---|---|---|---|
| H0: | No Association | 3 | −1267.30 | 0.00 |
| H1: | Markers Associated | 5 | −1122.84 | 288.92 |
| H2: | Markers and Disease Associated | 10 | −1035.84 | 462.93 |

Chi square probability = 0 to 20 decimal places.

Haplotype frequencies were estimated for both APOCI and APOE polymorphisms in patients (D) and control spouses (−). There was a very strong association between the two markers and the disease: $X^2(H_2)-X^2(H_1)=174$. This indicates that there is a very significant association of these genotypes with the disease.

Haplotype frequencies were also estimated individually for association with the disease. That for APOCI and the disease was $X^2=10.95$ (p=0.00419). That for APOE and the disease was 146.61 (p=0.0000). While this suggests a more significant association of the disease with APOE, both markers obviously are more significant than either one alone.

EXAMPLE 8

Further Polymorphisms for Analysis of Alzheimer's Disease

The present example provides for studies on two other polymorphisms in the coding region of the APOCI gene which were discovered by Southern blot hybridization. These polymorphisms will be examined to determine whether mutant alleles of these polymorphisms are also associated with Alzheimer's disease. Primers for amplification of regions containing the sites in question are provided to study the polymorphisms in relation to the disease. The sites in question are a BglI site and a DraI site.

The BglI site in APOCI is at position 673 of SEQ ID NO:7. The sense primer is preferably from about position 509 to about position 530 and the antisense primer is preferably from about position 1039 to about 1060. In particular, the primers were:

5' CTCCAGCAAGGATTCAGGTTGG (sense), SEQ ID NO:8

5' GGTCAGTGCTGAGTAAGGCAAT (antisense), SEQ ID NO:9.

These primers produce an amplified fragment having a size of about 551 bp. If the restriction site is present, the sizes of resulting fragments are about 387 and 164 bp. If the restriction enzyme site is absent, the fragment size will be about 551 bp. A digest of an amplified fragment from a heterozygote will have fragment sizes of about 551, 387, and 164 bp.

Four DraI sites are at positions 2318, 2767, 3037, and 4169 of SEQ ID NO:7. Primers for amplification of the region containing the first three DraI sites are preferably from about position 2157 to about position 2175, and from about position 3132 to about position 3150. In one aspect, the primers may be:

5' GTGTGTTTTTGGGTGGAGC (sense), SEQ ID NO: 10

5' CCTGTAACCCCACCACTTT (antisense), SEQ ID NO:11.

Amplification using these primers will produce a fragment of about 993 bp and when digested with DraI will produce fragments having sizes of about 2318, 449, and 270 bp if all three sites are present. If a site is absent, the sizes of the fragments will vary accordingly. Primers for the last DraI site are preferably from about position 3978 to about position 3996 and from about position 4258 to about position 4277. In particular, the primers may be 5' CAGGAGAATGGCTTGAACC (sense), SEQ ID NO:12, and 5' GGGTTCATGCCATTCTCCT (antisense), SEQ ID NO: 13.

Amplification using these primers will produce a fragment of about 299 bp and when digested with DraI will produce fragments of about 108 and 191 bp. If the site is absent the fragment size will be about 299 bp, and a heterozygote will have fragment sizes of about 299, 191, and 108 bp.

The BglI and DraI sites are in the coding region of the gene; mutations will undoubtedly affect amino acid composition and/or sequence. If an association of Alzheimer's disease with any of these sites exists, then the protein will undoubtedly be affected. The present inventor will be analyzing any effects that mutations in this region have on the protein ApoCI.

EXAMPLE 9

Analysis of the Upstream Regulatory Region

A 5500 bp regulatory region upstream from the APOCI gene is important in regulating the expression of ApoCI. The inventor has subcloned this region between the two genes and prepared a restriction fragment digested library. Relevant clones were identified after hybridization with antisense primes from the 5'region of APOCI and sense primers from the 3'region of APOE. These clones have been grown and the DNA extracted. These clones will be sequenced and the regulatory regions will be studied. Deletion studies will be conducted to determine those elements involved in regulation of APOCI and whether this region is affected in Alzheimer's disease.

Regulatory regions usually contain promoter and operator regions that are important in cis or trans control of the expression of genes. By constructing deletions in this region and fusing the product with a reporter gene, the function of different blocks of nucleotides within the regulatory region can be identified. The sequence of this regulatory region will be compared between an Alzheimer's patient and a person not having the illness to identify any sequence differences.

Variations found only in Alzheimer's patients may indicate abnormal regulation and/or accumulation of ApoCI and/or APOE proteins which, over time, may lead to neuronal cell death and the profound dementia found with this disease.

EXAMPLE 10

Identification of Peptide Encoded in the APOCI Region

The present inventor will screen the various peptides encoded by the coding regions of the APOCI gene, using as potential peptide fragments those encoded by regions located within the restriction sites noted in Example 8. It is contemplated that peptides other than the apolipoprotein E, or particularly potent fragments of the APOCI protein, may be identified using this approach. The existence of such a peptide is anticipated by the present inventor's studies provided herein.

These peptides may be used as a reference in the screening of biological samples for Alzheimer's disease. Elevated levels of the protein would be indicative of the disease. Antibodies, both monoclonal and polyclonal, may also be prepared using these peptides as immunogens. These antibodies may also be used in the screening of a patient biological sample for the presence of the peptide.

Peptide inhibitors for these identified peptides correlated with Alzheimer's disease are also contemplated, and provide an approach for treatment of Alzheimer's disease where increased levels of the peptide in a biological sample of an Alzheimer's patient are detected.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andrew, A. et al., *Clin. Genet.* 43 (1993) 286–294.
Caracciolo et al (1989) *Science*, 245:1107.
Chartier-Harlin M-C et al., *Hum Molec Gen*, 3 (1994) 569–574.
Corder, et al., (1993) *Science*, 261:921–923.
Dausset J. et al., *Genomics*, 6 (1990) 676–677.
Elston, R C and Johnson, W D. *Essentials of Biostatistics*, FA Davis Co. 1994
Farrer, L A and Cupples, L A. (1994) *Am. J Hum. Genet.* 54:374–383.
Frossard P M, et al., *Nucleic Acids Res.*, 15 (1987) 1344.
Frossard P M, et al., *Nucleic Acids Res.* 15 (1987) 1884.
Goddard, etal., *Am J. Hum. Genet.* 58 (1996) 1286–1302.
Grimberg J. et al., *Nucl Acids Res*, 17 (1989) 8390.
Hixson J E. and Vernier D T. *J Lipid Res*, 31 (1990) 545–548.
Kamino et al., (1996) *Gerontology* 42(Supl. 1):12–19.
Lauer S J, et al., *J Biol Chem*, 263 (1988) 7277–7286.
McKhann G. et al., *Neurology*, 34 (1984) 939–944.
Nillesen W M, et al., *Nucl Acids Res.* 18 (1990) 3428.
Rebeck G W, et al., *Neuron* 11 (1993) 575–580.
Saiki, et al., (1988) *Science* 239, 487–494.
Sanger, F. et al., *Proc Natl Acad Sci*, 74 (1977) 5463–5467.
Saunders A M, et al., *Neurology*, 43 (1993) 1467–1472.
Schellenberg G D, et al., *Ann Neurol*, 31 (1992) 223–227.
Sehayek E and Eisenberg S, *J Biol. Chem.* 266 (1991) 18259–18267.
Shulman, R S, et al., *J Biol Chem*, 250 (1975) 182–190.
Simonet W S, et al., *J Biol Chem*, 266 (1991) 8651–8654.
Smit et al., (1988) *Hum. Genet.*, 78:90–93.
Strittmatter W J, et al., *Proc Natl Acad Sci USA*, 90 (1993)1977–1981.
Strittrnatter W J, et al., *Proc Natl Acad Sci, USA* 90 (1993) 8098–8102.
Terwilliger, J D and Ott, J. Handbook of Human Genetic Linkage. Johns Hopkins Press, Baltimore (1994)
U.S. Pat. No. 4,683,202
U.S. Pat. No. 5,434,050
U.S. Pat. No. 5,441,870
Wall Street Journal, Aug. 15, 1995.
Weisgraber K H, et al., *J Biol Chem*, 265 (1990) 22453–22459.
Weiss, *Science*, 254 (1991) 1292
WO 95/16791

What is claimed is:

1. A method of screening for a genetic factor for having an enhanced risk of developing Alzheimer's disease comprising:

amplifying the genomic DNA encoding an APOCI region in a patient sample using a first oligonucleotide primer having a nucleotide sequence as in SEQ ID NO. 1 and a second oligonucleotide primer having a nucleotide sequence as in SEQ ID NO: 2;

incubating the amplified DNA with HpaI restriction enzyme for a time sufficient to allow cleavage; and determining a size of resultant restriction fragments, wherein the presence of a restriction fragment having a size of about 220 base pairs identifies a patient sample negative for the APOCI allele;

wherein the presence of a restriction fragment having the size of about 160 base pairs and a restriction fragment of about 60 base pairs identifies a homozygous APOCI allele profile and a 5-fold enhanced risk of having or developing Alzheimer's disease and a 2-fold enhanced risk for heterozygous allele profile; and wherein the presence of a restriction fragment having a size of about 220 base pairs, a restriction fragment having a size of about 160 base pairs, and a restriction fragment having a size of about 60 base pairs identifies a heterozygous APOCI allele and a 3-fold enhanced risk of having or developing Alzheimer's disease.

2. The method of claim 1 further comprising the steps of amplifying genomic DNA encoding an APOE region in the patient sample using at least one pair of APOE region-specific oligonucleotide primers;

incubating the amplified DNA with HpaI restriction enzyme, or isoschizomer thereof, for a time sufficient to allow cleavage; and determining the size of resultant restriction fragments, wherein a resultant restriction fragment of about 70 base pairs identifies a patient having an enhanced risk of having or developing Alzheimer's disease.

3. A method of screening for a genetic factor for an enhanced risk of developing Alzheimer's disease comprising:

amplifying genomic DNA encoding an APOC region in a patient sample using a first oligonucleotide primer having a nucleotide sequence as in SEQ ID NO: 3 and a second oligonucleotide primer having a nucleotide sequence as in SEQ ID NO: 4;

incubating the amplified DNA with HpaI restriction enzyme for a time sufficient to allow cleavage; and determining a size of resultant restriction fragments, wherein the presence of a restriction fragment having a size of about 270 base pairs identifies a patient sample negative for the APOCI allele;

wherein the presence of restriction fragment having a size of about 154 base pairs and a restriction fragment of about 95 base pairs identifies a homozygous APOCI allele profile and a 5-fold enhanced risk of having or developing Alzheimer's disease; and wherein the presence of a restriction fragment having a size of about 270 base pairs, a restriction fragment having a size of about 154 base pairs, and a restriction fragment having a size of about 95 base pairs identifies a heterozygous APOCI allele profile and a 3-fold enhanced risk of having or developing Alzheimer's disease.

4. The method of claim 3 further comprising the steps of:

amplifying genomic DNA encoding an APOE region in the patient sample using at least one pair of APOE region-specific oligonucleotide primers;

incubating the amplified DNA with HpaI restriction enzyme, or isoschizomer thereof, for a time sufficient to allow cleavage; and determining the size of resultant restriction fragments, wherein a resultant restriction fragment of about 70 base pairs, selected from the group consisting of a fragment having a size of about 270 base pairs, and a restriction fragment having a size of about 154 base pairs and a restriction fragment of about 95 base pairs identified a patient having an enhanced risk of having or developing Alzheimer's disease.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:1:

GAGCTCGGCT CTTGAGACAG GAA      23

(2) INFORMATION FOR SEQ ID NO:2:

(i) SEQUENCE CHARACTERISTICS:
      (A) LENGTH: 26 base pairs (B) TYPE: nucleic acid
        (C) STRANDEDNESS: single
        (D) TOPOLOGY: linear (xi) SEQUENCE DESCRIPTION: SEQ ID NO:2:

GGTCCCGGGC ACTTCCCTTA GCCCCA                                                    26

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

CATCCCCTGC TTGTTCAATC G                                                         21

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

CACTCTCACC TCTCAATCTT CC                                                        22

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

ACAGAATTCG CCCCGGCCTG GTACAC                                                    26

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

TAAGCTTGGC ACGGCTGTCC AAGGA                                                     25

(2) INFORMATION FOR SEQ ID NO:7:

(i) SEQUENCE CHARACTERISTICS:
        (A) LENGTH: 5375 base pairs
        (B) TYPE: nucleic acid
        (C) STRANDEDNESS: single
        (D) TOPOLOGY: linear (xi) SEQUENCE DESCRIPTION: SEQ ID NO:7:

GCATGCAGCC CCCAGTCACG CATCCCCTGC TTGTTCAATC GATCACGACC CTCTCACGTG        60

CACCCACTTA GAGTTGTGAG CCCTTAAAAG GAACAGGGAT TGCTCACTCG GGGAGCTCGG       120

CTCTTGAGAC AGGAATCTTG CCCATTCCCC GAACGAATAA ACCCCTTCCT TCGTTAACTC       180

AGCGTCTGAG GAATTTTGTC TGCGGCTCCT CCTGCTACAT TCTGAGTGGG GGAAAGGGAC       240

TAAGGTGGTC TGAGGACCCC ACAGAGTCAG GAAGATTGAG AGGTGAGAGT GCTGAACGGG       300

GAGGGGCTTT GGGGCTAAGG GAAGTGCCCG GGACCCCACC TGACCCCAAC GCTCACGGGA       360

CAGGGGCAGA GGAGAAAAAC GTGGGTGGAC AGAGGGAGGC AGGCGGTCAG GGGAAGGCTC       420

```
AGGAGGAGGG AGATCAACAT CAACCTGCCC CGCCCCTCCC CAGCCTGATA AAGGTCCTGC    480

GGGCAGGACA GGACCTCCCA ACCAAGCCCT CCAGCAAGGA TTCAGGTTGG TGCTGAGTGC    540

CTGGGAGGGA CACCCGCCTA CACTCTGCAA GAAACTCAAA AAGGGAGATG AGGGGATCGT    600

GGGAGGGAGG TAGGGAGGGA GGAGGGTGCC ACTGATCCCC TGAACCCCTG CCTCTGCCTC    660

CAGAGTGCCC CTCCGGCCTC GCCATGAGGC TCTTCCTGTC GCTCCCGGTC CTGGTGGTGG    720

TTCTGTCGAT CGTCTTGGAA GGTAAAAGTG GGATGGGAGA ATTGGGGAGT TTGGAGATTT    780

GGAAGAGTGA AGGTGGCTAC AGGCCTGGGG TCCCGGCTTA GAGGACCTCT GAGAGCTCCG    840

GGGCCCCTTC TGGGTCGTGG TTGCCTCATC GTGGTCGGGT GGGTCTCCAG GTTCTCCCAG    900

GCTCAGTCCC GCAGGCGCCA AATCTGCGCA GGAGAGCACT AGCAACCGAT GACGTATTGA    960

GGCCCACACC TCTGGGATTG GCTGTCCTGC TTCGACAGCC TTGAAAGTGG GTAAGCTGGG   1020

TGGGGGGCTC TGGGAGAGGT CAGTGCTGAG TAAGGCAATT CCCAGCAGCT TGAGCCCCAC   1080

CAGGTCACTC CAGTATTCCT CCCCATTCTT TTTTTTTTTT TTTTTTTTTC TCTTGAGACG   1140

GAGTCTCGCT CTGTCGCCGA GGCTGGAGTG CAGTGGCGCG ATCTCGGCTC ACTGCAAGCT   1200

CCGCCTCCCT GGTTCACGCC ATTCTCCTGC CTCAGCAGGA CTACAGGCGC CCGCCTCCGC   1260

GCCCGGCTAA TTTTTTGTAT TTTCAGTAGA GACAGGGTTT CACCGTGGTC TCGATCTCCT   1320

GACTTTGTGA TCCGCCTGCC TCGACCTCCC AAAGTGCTGG GATTACAGGC GTGAGCCACC   1380

GCGTCCGGCC ATTCCTCCCC ATTCTAACCA CATGATCCCC AAGGATCTCT ATCCATCCCG   1440

GTATCCCAAC CTAAGGGGGT TCCAATAACA AATTTTTGGC CGGGCAGGGT GGCTCATGCC   1500

TGTAATCCCA GCACTTTGGG AGGCCGAGGC GGGCAGATCA CTTGAGGTCA GGAGTTCAAA   1560

CCAGCCAGGC CAACATGGTG GAAACTTCGT CTCTAGCTAA AAATACAAAA AAATTAGGCC   1620

AGGTGTGGAG GCACGCGCCT GTAGGCCCAG CTACTCGGGA GGCTGAGGCA GGAGAATCAC   1680

TTGAACCCGG GAGGCGGAGG TTGCAGTGAG CCGAGATCAT ACCACTGCAC TCCAGCCTGG   1740

CTGACACAGC AAGACTCCGT CTCAAAACAA AACAAAACAA AAATAGGCTG GGTGTGGTGG   1800

TGCACACCTG TAATCCCAGC TACTTGGGAG GCTGAGGCAG GAGAACTGCT TGAACCCGGG   1860

AGGTGGTGGT TGCAGTAGGC CGAGATCATG CCACTGCACT CCAGCTTGGG CTACAGAGCA   1920

AGACTCCATC TCCAAAAAAA AAAAAAAAAA AACAAATTTT GAACCCCTGC CCATCTTCCT   1980

GGCAGGCCCA GCCCCAGCCC AGGGGACCCC AGACGTCTCC AGTGCCTTGG ATAAGCTGAA   2040

GGAGTTTGGA AACACACTGG AGGACAAGGC TCGGGAACTC ATCAGCCGCA TCAAACAGAG   2100

TGAACTTTCT GCCAAGATGC GGTTAGAACC CTTCCCAGGG CACGGGAGAG CTGGGGTGTG   2160

TTTTTGGGTG GAGCCCTGGC AGATGGTCCA AGATGAACAG ATTGAAAAAA AAACAAGTCC   2220

TGGAGAGGCT GACAACATCC CTCTGGTCAC ACAGCTAGAT CTCAAGGTGC TCAGACTTCA   2280

AGGACAGTTT CCCTGACTCC CATCCAGGCC ATATTTTAAA AGATGGTCTT GGGCTGGGCA   2340

CGGTGGCTCA TGCTTGCAAT CCCAGCACTT AGGGAGGCCG AGGTGGGCTG ATTGCCTGAG   2400

GTCAGGAGTT CGAGACCAGT CTGACCAACA TCGGTGAAAT CTTAGTCTCT ACTAAAAATA   2460

CAAAAAATT ACGGCAGGCA TGGTGGCGTG CACTGTAATC CCAGCTAGTC GGGAGGCTGA   2520

GGCAGGGGAA TTGCTTGAAC CAGGAAGGTG GGAGTTACAG TGAGCCAACA TTGTGCCAGC   2580

CTGGGTGACA GAAGGAGACT CTGTCTCAAA AAAAAAAAA AAAAAAAAAA AAAACAAGAT   2640

GGTCTTGCCC AGGAATGGTG GCTAACACCT GTAATTCCAG CATTATGGGA GGCTGAGATG   2700

GGAGGATTGC TTGAGCCCAG GAGTTCGAGA CCAGCCTGAC CAACATGGCG AGATCCTGTC   2760
```

```
TCCATTTAAA AAAAAAAAAA AAAAGATGGT TTTGTGAGGT AATGAAAATG AAGGCCCCAA    2820

GCTTGGCCAG ACCTGGGTCC CCAGGCTGGA GTAGCACCCC TTCCTGTGTG ATCTTGACAG    2880

AGGGGCATTA CTGTGAGCCT CAGTTTCCTC TCCTATAAAC TGGTGGTTCT ACAGGGAAGT    2940

AAAGGAGCAG GCCTACAGGG TGTCTGGTAC ATGTAGATGC TCAGTATATC ATTAAACCAC    3000

CTTCCCCTTT GCAAGTTAGA GAGTCATTTG TTCTTTAAAA AATATTTTAC TGAGCATCTG    3060

CTAAGTGCTG GAAAACTCTT TCAATGTGGG GAATAAAACA GTGAAGAACT GCCGAGCACG    3120

GTGGCTCACA CCTGTAACCC CACCACTTTG GAAGGCCGAG GTGGGTGGAT CACTTGAGGT    3180

CAGGAGTGCG AGAACCCCGT CCCTAATAGA AATGCAAAAA AAATTAGCTG GGCATGGTGG    3240

CCCATGCCTG TAGTCCCAGC TCCTTGGGAG GGCTGAGGCG GAGAGGATTG CTTGAGCCCA    3300

GGAGATCTAG GCTGCAGTGC GCCATGTTTG TGCCACTGCA TTCCAGCCTG GGTAACAGAA    3360

TGAGACCCTG TCTCAACAAA AAAAGAAAAG AAAAGAGAAG AAAAGAGAAA AGAAAGACAG    3420

GGAGGGAGGG AGGAAGGAAG GGAGGGAGGG AGGGAAAATA GAGCCAGGCA TAAACTTAGA    3480

AAGATCGTTT GGAGGCCAGG CACAATGGCT CACACCTGTA ATCCCAGCAC TTTGGGAGGC    3540

CAAGGCAAGC AGATCAACTG AGGTCAGGAG TTCGAGACCA GCCTAACATG GAGAAAACCC    3600

CTGTCTCTAC TAAAAAAAAA TACAAAAAAA TTAGCCGGGG CGTGGTGCAT TCCTGTAGTC    3660

CTAGCTACTC GGGAGCCTGA GGCAGGAGAA TCACTTGAAC CCGGGAGGCG GAGGTTGCAG    3720

TGAGCCGAGA TCATGCCACT GCACTCCAGC CTGGGCGACA AGGCGAGACT CCATGCCAAA    3780

AAAGAAAAAA AACTCCTGGC GCGGTGGCTC ACGCCAGTAA TCCCAGCACT GTGGGAGGCT    3840

GAGCAGGCGG ATCACGAGGT CAGGAGTTCG AGACTAGCCT GCTCAACATA ATGAAACCCT    3900

CTCTGTACTA AAAATACAAA AATTAGCTGG GTGTGGTGGC AGGCACCTGT AGTCCCAGCT    3960

ACTCGGGAGG CTGAGGCAGG AGAATGGCTT GAACCTGGGA GGCAGAGGTT GCAGTGAGCC    4020

GAGACAGTGC CATTGCACTC CAGTCCAGGT GACAGAGCGA AACTCCATCT CAAAAAAAAA    4080

AGGAAGGCAT TGGTAGCAAG AGATGGCAGG CCTTGAAAGC CAGGCCAGGG TGAAGTGTTT    4140

CTTTTTTTTT TTTTTTTTTT TTCTTTTTAA ATTTTTTTTT TTGAGACGGA GTCTCGCTCT    4200

GTCACCCAGG CTGGATTGCA GTGGCCTGAT CTCGGCTCAC TGCAAGTTCC GCCTCCCGGG    4260

TTCATGCCAT TCTCCTGCCT CACCCTCCCG AGTAGCTGGG ACTACAGGCA CCTGCCACCA    4320

GGCCAGCTAA TTTTTTGTAT TCTTAGTAGA ATGTAGAATT TACTTAGTAG AATTTTTTGT    4380

ATTCTTAGCC AGCATGGTCT CGATCTCCTG ACCTGGGTGA TCCACCCGCC TCGGCCTCCC    4440

AAAGTGCTGG GATTACAGGC GTGAGCCACG GCGCCCGGCC TTATTTTTTC TTTTTGAGAT    4500

GTACCCAGAC TGGAGTACAG TGGTGCGATC TCGGCTTACT GGAACCTCCA CCTCCCGGGT    4560

TCAGGCAATT CTCCTGCCTC AGCCTCATGA GTACTTGGAA CTACAGGTGT GTGACACCAC    4620

ACATGGTATT TTTTGTATTT TTAGTGAAGA TGACATTTCA CCATGTTGCC CAGGTTGGTC    4680

TCGAACTCCT GACCTCAAGT GATCAGCCTA CCTCGGCCTC CCAAAGTGTT GGGATTACAG    4740

GCGTGAGCCA AATGCCCAGC CAAGGGTAAA GTGTTTAGAC TTAAAGTGCT TTGGTCCATC    4800

TGGGAAACTG AGGCAGAGAA GTTGGCCCAC CCAGCCCAGC GGTCCTCCTA ATCCCACAGA    4860

CAGTGGGGAT GGAGATTCTG CAAGGGGAAG AGGTGGGAGT CAGGTAGCAG GCAGAATTTG    4920

GACAGCCTGG GAAGTAGCTG CACACAGTGA CCCCCTTCCT TATTCCTCCC CACAGGGAGT    4980

GGTTTTCAGA GACATTTCAG AAAGTGAAGG AGAAACTCAA GATTGACTCA TGAGGACCTG    5040

AAGGGTGACA TCCCAGGAGG GGCCTCTGAA ATTTCCCACA CCCCAGCGCC TGTGCTGAGG    5100

ACTCCCTCCA TGTGGCCCCA GGTGCCACCA ATAAAAATCC TACAGAAAAT TCTCTCCTGA    5160
```

```
GTGCTTCTTT ACTCTGGGGA AGGGGCTGCG GGAGAGGGTA GGGGCTTCCA GAGAGGGCAG      5220

GGTCTGCAGC CACTGTGGAA AAACAGTATG GGGTTTCCTC AAAACATTAA AGATAGAACT      5280

CTCAAATGAT CCTTCAATCC CACTTCTGGG TATTTATTCA AAAGAATTGA AATCAGGACC      5340

TTGAAGAGAT ACCTGCCCTC CCATGTTCAC TGCAG                                5375
```

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:8:

```
CTCCAGCAAG GATTCAGGTT GG                                                22
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

```
GGTCAGTGCT GAGTAAGGCA AT                                                22
```

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:10:

```
GTGTGTTTTT GGGTGGAGC                                                    19
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:11:

```
CCTGTAACCC CACCACTTT                                                    19
```

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:12:

```
CAGGAGAATG GCTTGAACC                                                    19
```

(2) INFORMATION FOR SEQ ID NO:13:

(i) SEQUENCE CHARACTERISTICS:
        (A) LENGTH: 19 base pairs

-continued

```
        (B) TYPE:  nucleic acid
        (C) STRANDEDNESS:  single
        (D) TOPOLOGY:  linear (xi) SEQUENCE DESCRIPTION:  SEQ ID NO:13:

GGGTTCATGC CATTCTCCT                                                        19
```